US00PP09379P

United States Patent [19]

VandenBerg

[11] Patent Number: Plant 9,379

[45] Date of Patent: Nov. 21, 1995

[54] CHRYSANTHEMUM PLANT NAMED 'YVETTE'

[75] Inventor: Cornelis P. VandenBerg, Salinas, Calif.

[73] Assignee: Yoder Brothers, Inc., Barberton, Ohio

[21] Appl. No.: 331,865

[22] Filed: Nov. 1, 1994

[51] Int. Cl.[6] ..... A07H 5/00

[52] U.S. Cl. ..... Plt./82.1

[58] Field of Search ..... Plt./82.1, 82.2, Plt./74.1

[56] References Cited

U.S. PATENT DOCUMENTS

| | | | |
|---|---|---|---|
| Plt. 5,491 | 6/1985 | Shoesmith et al. | Plt./82.1 |
| Plt. 5,934 | 4/1987 | Shoesmith | Plt./82.1 |
| Plt. 6,836 | 6/1989 | Hesse | Plt./82.1 |
| Plt. 7,516 | 5/1991 | VandenBerg | Plt./82.1 |

*Primary Examiner*—Howard J. Locker
*Attorney, Agent, or Firm*—Foley & Lardner

[57] ABSTRACT

A Chrysanthemum plant named Yvette particularly characterized by its flat capitulum form; anemone capitulum type with a small anemone cushion; white ray floret color with yellow anemone cushion; diameter across face of capitulum of 29 to 35 mm when fully opened, when grown as a pinched spray pot mum; very floriferous with excellent display of many small flowers; photoperiodic flowering response to short days of 50 to 57 days; plant height with 15 long days after sticking unrooted cuttings prior to start of short days and with 0 to 1 application of 2500 ppm B-9 SP, ranges from 18 to 23 cm when grown as a pinched pot mum with 4 cuttings in a 15 cm pot; small dark green foliage; branching pattern is spreading and prolific, each plant having 5 to 8 laterals after pinch; and recommended as a spray pot mum.

3 Drawing Sheets

The present invention comprises a new and distinct cultivar of Chrysanthemum, botanically known as *Dendranthema grandiflora,* and referred to by the cultivar name Yvette.

Yvette, identified as 4680 (89-195001), was originated from a cross made by Cornelis P. VandenBerg in a controlled breeding program in Salinas, Calif., in 1989.

The female parent of Yvette was an unnamed seedling, identified as 86-669007, and described as a coral-pink spray pot mum with a flat capitulum form; anemone capitulum type with a small anemone cushion; diameter of capitulum of 38 to 50 mm; flowering response to short days of 48 to 56 days; plant height of 20 to 30 cm when grown as a pinched spray pot mum with 4 cuttings in a 15 cm pot, with 15 to 23 long days after sticking unrooted cuttings prior to start of short days and 1 to 2 applications of 2500 ppm B9 SP; and a spreading and prolific branching pattern, with 4 to 6 branches developing per plant after pinch. The female parent was discarded from all programs in June 1991.

The male parent of Yvette was an unnamed seedling, identified as 86-664003, and described as a flat daisy spray pot mum with a yellow ray floret color; diameter of capitulum of 41 to 51 mm; flowering response to short days of 48 to 54 days under normal conditions; plant height of 23 to 28 cm with 15 to 16 long days after sticking unrooted cuttings prior to start of short days and 1 to 2 applications of 2500 ppm B-9 SP; and a spreading and prolific branching pattern, with 5 to 7 breaks developing per plant after pinch. The male parent was discarded from all programs in August 1989.

Yvette was discovered and selected as one flowering plant within the progeny of the stated cross by Cornelis P. VandenBerg in Apr. 1990, in a controlled environment in Salinas, Calif.

The first act of asexual reproduction of Yvette was accomplished when vegetative cuttings were taken from the initial selection in Jun. 1990 in a controlled environment in Salinas, Calif., by technicians working under supervision of Cornelis P. VandenBerg.

Horticultural examination of controlled flowerings of successive plantings has shown that the unique combination of characteristics as herein disclosed for Yvette are firmly fixed and are retained through successive generations of asexual reproduction.

Yvette has not been observed under all possible environmental conditions. The phenotype may vary significantly with variations in environment such as temperature, light intensity and daylength, without, however, any variance in genotype.

The following observations, measurements and comparisons describe plants grown in Salinas, Calif. under greenhouse conditions which approximate those generally used in commercial greenhouse practice.

The following traits have been repeatedly observed and are determined to be basic characteristics of Yvette, which, in combination, distinguish this Chrysanthemum as a new and distinct cultivar:

1. Flat capitulum form. 2. Anemone capitulum type with a small anemone cushion.

3. White ray floret color with yellow anemone cushion.

4. Diameter across face of capitulum of 29 to 35 mm when fully opened, when grown as a pinched spray pot mum.

5. Very floriferous with excellent display of many small flowers.

6. Photoperiodic flowering response to short days of 50 to 57 days.

7. Plant height, with 15 long days after sticking unrooted cuttings prior to start of short days and with 0 to 1 applications of 2500 ppm B-9 SP, ranges from 18 to 23 cm when grown as a pinched pot mum with 4 cuttings in a 15 cm pot.

8. Small dark green foliage.

9. Branching pattern is spreading and prolific, each plant having 5 to 8 laterals after pinch.

10. Recommended as spray pot mum.

The accompanying photographic drawings show typical inflorescence and leaf characteristics of Yvette, with the colors being as nearly true as possible with illustrations of this type.

Sheet 1 is a color photograph of Yvette grown as a pinched spray pot mum with 4 cuttings in a 15 cm pot.

Sheet 2 is a black and white photograph of three views of the inflorescence of Yvette.

Sheet 3 is a black and white photograph showing the upper and under sides of the leaves of Yvette at 3 stages of development (mature, intermediate and immature).

In sheets 2 and 3, a measuring tape in centimeters has been added.

Of the commercial cultivars known to the inventor, the most similar in comparison to Yvette is the commercially available but unpatented cultivar identified as Celeste. Reference is made to attached Chart A, which compares certain characteristics of Yvette to the same characteristics of Celeste.

The branching pattern of both cultivars is similar. Ray floret color of both cultivars is white, with Celeste showing a slight pinking of the underside of the ray florets. The flowering response to short days of both cultivars is in the same range, with Celeste having a slightly faster flowering response in some flowering trails. Yvette has a small anemone cushion, while Celeste has a daisy capitulum type. Yvette also has a smaller diameter of capitulum and a shorter plant height when compared with Celeste.

In the following description, color references are made to The Royal Horticultural Society (R.H.S.) Colour Chart. The clear white color of the ray florets of Yvette is not represented in the R.H.S. Colour Chart. The color values were determined on plant material grown as a pinched spray pot mum in Salinas, Calif. on Aug. 5, 1994.

Classification:

*Botanical.*—*Dendranthema grandiflora* cm Yvette.

*Commercial.*—Anemone spray pot mum.

INFLORESCENCE

A. Capitulum:

*Form.*—Flat.

*Type.*—Anemone with small cushion.

*Diameter across face.*—29 to 35 mm when fully opened.

B. Corolla of ray florets:

*Color (general tonality from a distance of three meters).* White.

*Color (upper surface).*—Clear white.

*Color (under surface).*—Clear white.

*Shape.*—straight, flat. Apex rounded.

C. Corolla of disc florets:

*Color (mature).*—12A.

*Color (immature).*—12A, overlaid with 144C.

D. Reproductive organs:

*Androecium.*—Present on disc florets only; scant pollen.

*Gynoecium.*—Present on both ray and disc florets.

PLANT

A. General appearance:

*Height.*—18 to 23 cm when grown as a pinched pot mum in a 15 cm pot with 15 long days after direct sticking unrooted cuttings and 0 to 1 application of 2500 ppm B-9 SP.

*Branching pattern.*—Spreading and prolific, with 5 to 8 laterals after pinch.

B. Foliage:

*Color (upper surface).*—147A.

*Color (under surface).*—147B.

*Shape.*—Deeply lobed and slightly serrated.

CHART A

| CHARACTERISTICS | YVETTE | CELESTE |
|---|---|---|
| Ray floret color | White with yellow cushion | White with slight pink underside |
| Capitulum form and type | Flat anemone | Flat daisy |
| Diameter across face of capitulum | 29 to 35 mm | 38 to 48 mm |
| Flowering response | 50 to 57 days | 47 to 57 days |
| Plant height with 14 to 17 long days | 18 to 23 cm | 20 to 28 cm |
| Branching pattern | Spreading 5 to 8 laterals | Spreading 5 to 8 laterals |

COMPARISONS MADE OF PLANTS GROWN AS PINCHED SPRAY POT MUMS IN SALINAS, CALIFORNIA

I claim:

1. A new and distinct Chrysanthemum plant named Yvette, as described and illustrated.

* * * * *

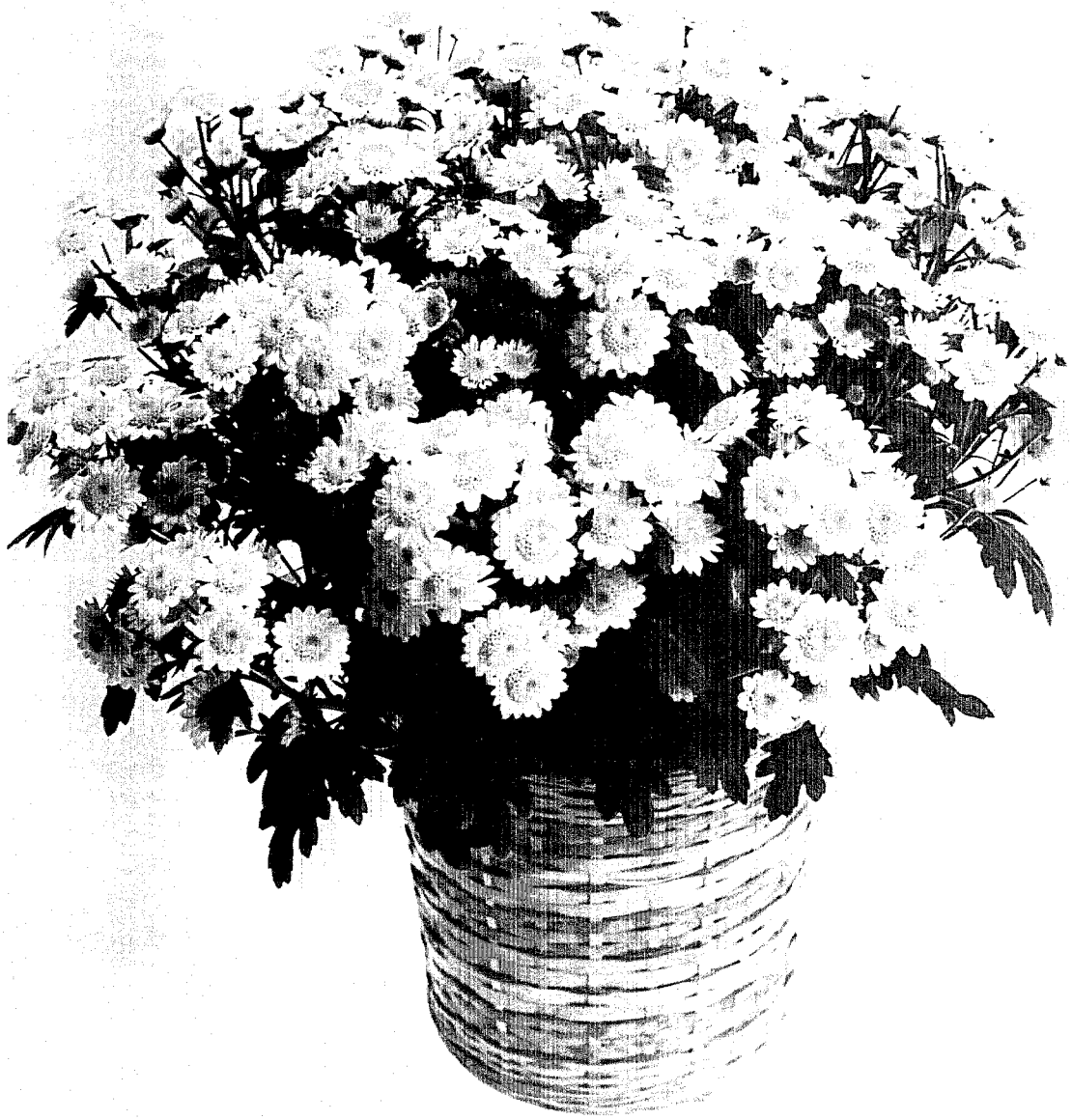

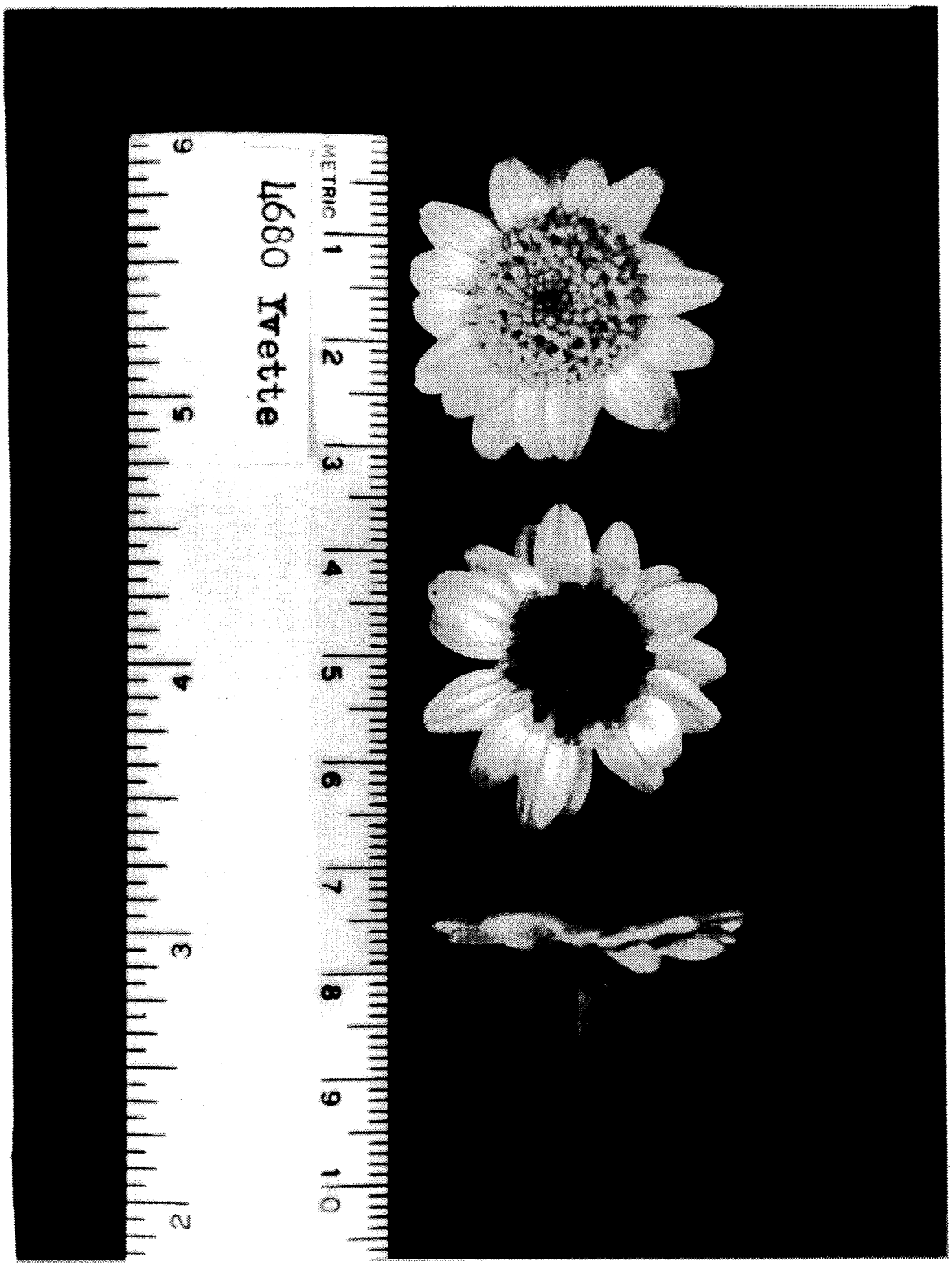
METRIC
1680 Yvette

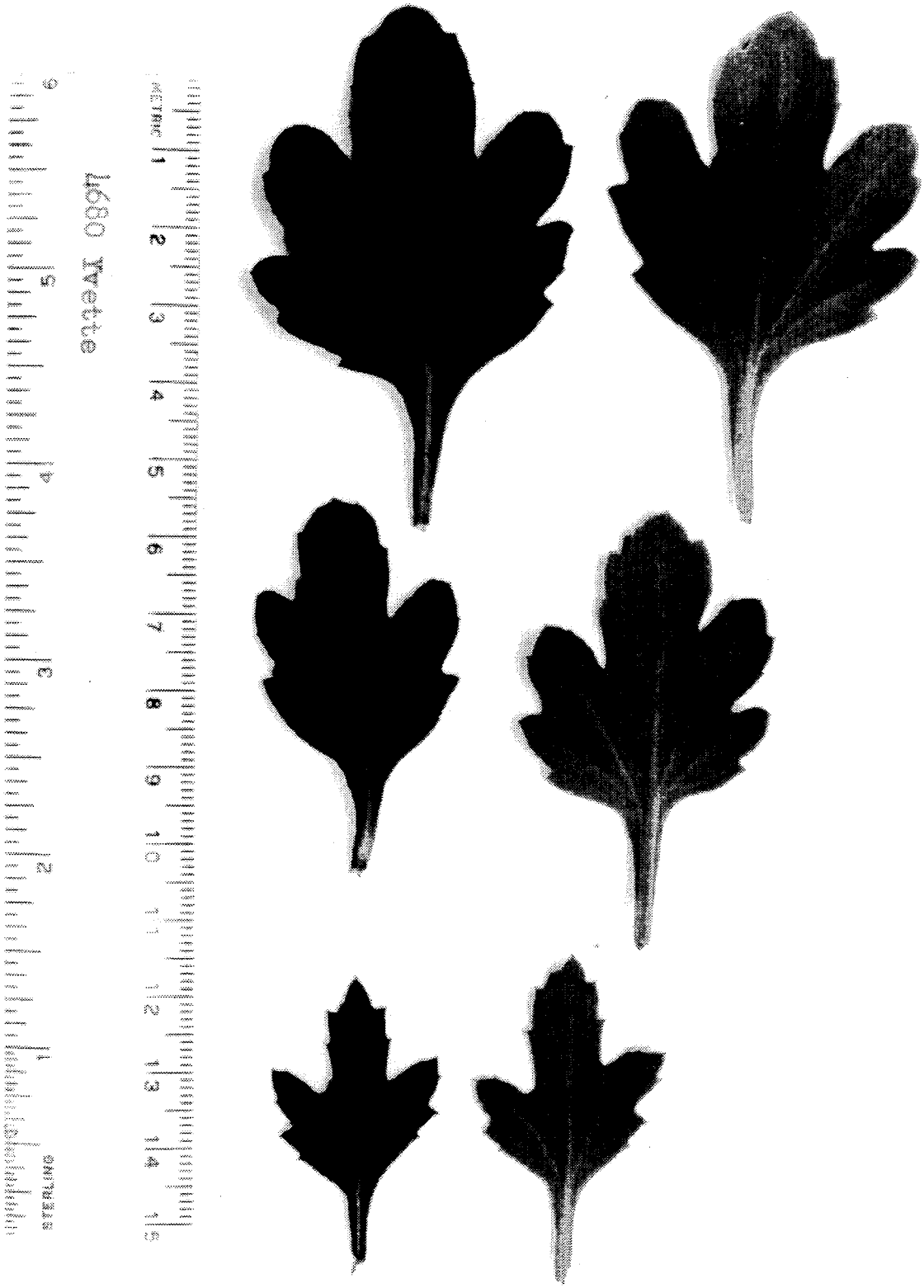
1680 Yette